United States Patent [19]

Scheunemann

[11] Patent Number: 4,772,203
[45] Date of Patent: Sep. 20, 1988

[54] IMPLANT AND METHOD FOR USING SUCH IMPLANT

[76] Inventor: Rüdiger Scheunemann, Karpenbachweg 13, D-5204 Lohmar-Donrath, Fed. Rep. of Germany

[21] Appl. No.: 795,494
[22] PCT Filed: May 4, 1985
[86] PCT No.: PCT/EP85/00196
   § 371 Date: Oct. 24, 1985
   § 102(e) Date: Oct. 24, 1985
[87] PCT Pub. No.: WO85/05026
   PCT Pub. Date: Nov. 21, 1985

[30] Foreign Application Priority Data

May 8, 1984 [DE] Fed. Rep. of Germany ....... 3416872
Jun. 27, 1984 [DE] Fed. Rep. of Germany ....... 3423667

[51] Int. Cl.⁴ .............................................. A61C 8/00
[52] U.S. Cl. ................................... 433/173; 433/201.1
[58] Field of Search ............... 433/173, 174, 175, 176, 433/201; 128/92 YO; 623/16

[56] References Cited

U.S. PATENT DOCUMENTS

| 4,051,598 | 10/1977 | Sneer | 128/92 C |
| 4,495,664 | 1/1985 | Blanquaert | 128/92 YO |

FOREIGN PATENT DOCUMENTS

| 0024008 | 2/1981 | European Pat. Off. | 433/173 |
| 0023608 | 2/1981 | European Pat. Off. | 433/173 |
| 0094829 | 3/1983 | European Pat. Off. | 128/92 A |
| 2414460 | 10/1975 | Fed. Rep. of Germany | 433/173 |
| 2502884 | 7/1976 | Fed. Rep. of Germany | 128/92 YO |
| 2628284 | 1/1977 | Fed. Rep. of Germany | 128/92 YO |
| 2611744 | 9/1977 | Fed. Rep. of Germany | 433/173 |
| 2620907 | 11/1977 | Fed. Rep. of Germany | 128/92 YO |
| 2491326 | 4/1982 | France | 433/201.1 |

OTHER PUBLICATIONS

Münch, M., "Operating Instructions for the Immediate Implant According to M. Münch", Nürtingen, West Germany (1983), pp. 10, 11.

Primary Examiner—John J. Wilson
Attorney, Agent, or Firm—Spencer & Frank

[57] ABSTRACT

In order to extend durability and long-term use of bone, joint and tooth root implants, the previously limited-time implants are replaced by metallic or composite fiber implants for bone and tooth root replacement having a partially or completely resorbable matrix on the side of the bone. On the side of the bone, the matrix is composed of organic and/or inorganic materials which are resorbed after the implantation and are replaced by natural bone. This produces a bond free of connective tissue between the bone and the remaining structure, assuring a physical friction fit. The remaining structure is firmly bonded to the core of the implant.

34 Claims, 2 Drawing Sheets

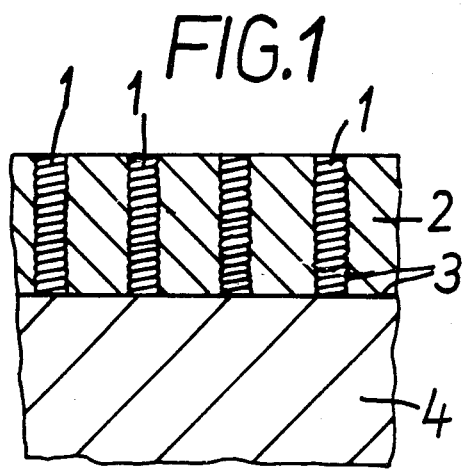
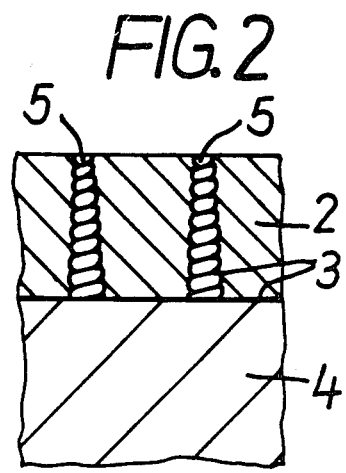
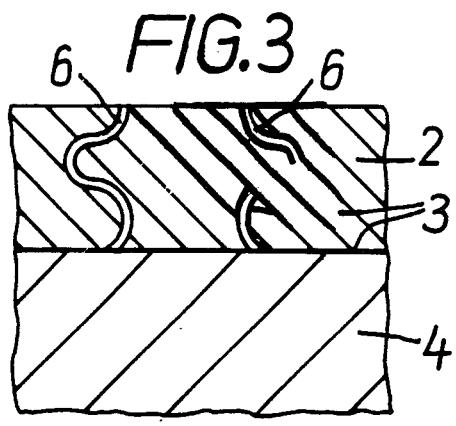
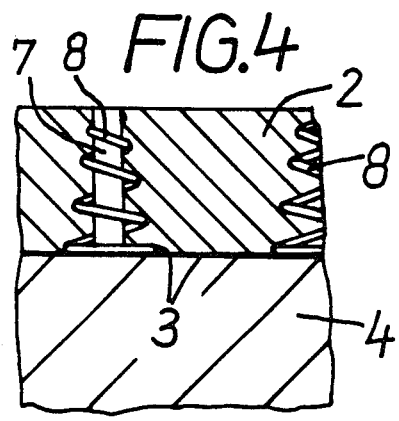
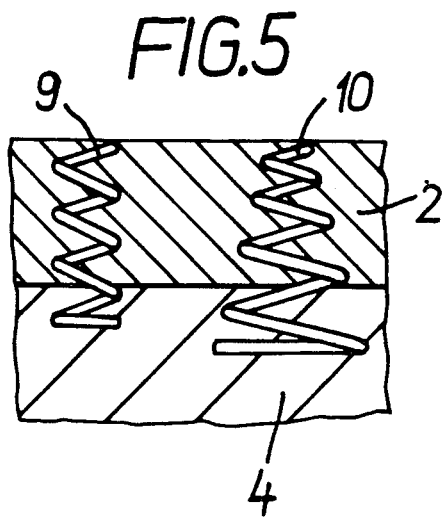
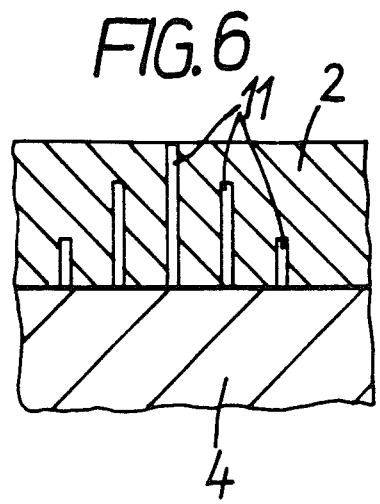

IMPLANT AND METHOD FOR USING SUCH IMPLANT

BACKGROUND OF THE INVENTION

1. Field of the invention

The invention relates to an implant for bone and tooth root prostheses, the implant being composed of a core and a matrix having particles embedded therein. Joint implants are addressed in particular. The invention further relates to a method using the implant according to the invention.

2. Background of the Art

It is known that metallic, ceramic and bonded fiber implants are being used, or their use is being developed as substitutes for bones and joints or tooth roots. Some of the materials employed are bio-inert, some are biocompatible. In many cases it is desired to provide coatings of inorganic and organic substances having bioactive effects. These coating materials are more or less resorbable and are dissolved by the body in a few years at the latest. Since growth and attachment by bone growth occurs only at the surface of the implant, loosening phenomena occur in all known implant materials.

For tooth root implants the state of the art permits only a rigid connection between implant and jaw bone. There are no dental implants which are adapted to natural conditions. Therefore, complicated structures to dampen pressure peaks are required for present-day dental implants to prevent the implant from breaking out of the jaw bone. Due to the wrong stresses on the jaw bone, the latter also decomposes if commercially available implants are employed.

Implants are also known which are made of porous, tissue compatible metals, plastic fibers or composite metals and in which the outer layers contain a plastic matrix with embedded inorganic, resorbable particles. However, in connection with these prior art implants it has also been found that an uninterfered-with bond between bone and fiber material is impossible. The consequence is that after a certain period of time, the implants must be exchanged for new ones which usually requires, in a then necessary second surgical procedure, further excavation of bone, e.g. longer shafts or larger hip sockets.

It is therefore the object of the invention to provide an implant which assures a permanent and lifetime connection, or anchorage, of the implant with the natural bone and thus reduces or completely avoids repeated surgery for implantations. It is a further object of the present invention to provide a suitable method which employs implants that accomplish this task.

SUMMARY OF THE INVENTION

This is accomplished by an implant whose core is made of metal or a composite material and is provided with a transition structure at the side of the bone wherein the matrix surrounds porcupine quill or brushlike flexible metallic wires or flexible fibers, particularly in the form of springs (helixes) which end preferably perpendicularly to the implant surface and are permanently anchored in the core. Depending on the type of use, the wires or fibers may be disposed at an oblique angle or perpendicularly to the implant surface. Preferred are wires or fibers in the form of helixes. The wires or fibers fixed to the implant core are of such consistency that their modulus of elasticity (E modulus) essentially corresponds to that of the tissue that will later surround the surface matrix. In this way, the wires or fibers in the bone bond meet two conditions even under stresses of all types, such as tension, pressure, bending, torsion and shear forces:

1. it is assured that the load is distributed essentially uniformly over the length of the fiber or the wire from the end of the fibers or wires to the implant core;

2. no or only slight micromovement or relative movement is produced between the fibers or wires and the bone or the bone cells. Additionally, the wires and fibers, respectively, increase the area of adhesion between bone and implant.

According to a further feature of the invention, the matrix is completely or partially resorbable on the bone side and is preferably composed entirely or partially of natural bone substance. Suitable implant materials are body compatible organic, inorganic substances, or mixtures thereof; resorbable substances are particularly those which are bioactive and/or osteogenesis inducing, such as, for example, tricalcium phosphate, hydroxylapatite and bioglasses.

The use of such an implant having the described special transition structure and, preferably on the side of the bone, a partially or totally resorbable matrix of organic and/or inorganic bioactive and/or osteogenesis inducing materials which are resorbed after the implantation and replaced by natural bone, assures a permanent (lifelong) bond or anchorage, respectively, of the implant to the natural bone. These wires or fibers are enclosed tightly by the bone without connective tissue, particularly if the thickness of the wires or fibers is less than 800 $\mu$m. This results in a natural bond between bone and implant. Preferably, wires or fibers are employed which essentially have uniform tension and strength over their length.

After their implantation, the fibers or wires, which—from a rigid anchorage—project individually or in groups from the implant core like brushes or porcupine quills, are totally or partially encased by the bone without connective tissues. If the anchorage is elastic, as for example for dental implants, a layer of connective tissue is formed between the fibers or wires, respectively. For example, for the replacement of tooth roots, the special tooth holding apparatus of the natural tooth is simulated by fibers or wires having an adapted E modulus and constituting an elastic connection between the tooth root implant and the jaw bone after the jaw bone has grown around the transition structure. A layer of connective tissue is formed between the implant core and the bone tissue.

The structure of the fibers or wires may be helical or wavy. In any case, the wires or fibers are flexible and are adapted to the rigidity of the bone. If the helical shape is selected, a further feature of the invention provides that the helix may be cylindrical, conical or parabolic and may preferably have a pitch which is equal to or greater than the diameter of the helical wire.

For cylindrical helixes, a constant bending stress over their length is accomplished in that the thickness of the helical wire decreases toward the tip of the helix. For conical or parabolic helix cross sections, the thickness of the helical wire may also be varied. If necessary, it is further possible, in order to absorb shear forces, to provide the helix with a core which is firmly connected with the implant core. Between helix and core there preferably exists no firm connection on the side of the bone.

The materials and geometry of the helix thus adapt the moduli of elasticity between bone tissue and helix by selection of the spring constants. In this way, no micromovement results between spring (helix) and the contacting bone when there are stresses on the bone and on the implant, e.g. alternating bending stresses.

With the wavy fiber or wire structure, uniform strength is realized by different fiber geometries in the fiber itself or with respect to adjacent fibers and by different fiber materials. The fibers or wires, respectively, are preferably arranged to be offset with respect to one another.

Since generally the helical or fibrous structures are able to absorb and transfer forces only after the bone tissue has grown in, it is preferably possible to fill the interstices between the wires or fibers with a wholly or partially resorbable bioactive and/or osteogenesis inducing material. The substance introduced into the implant on the side of the bone is wholly or partially resorbed by physiological influence and is replaced by natural bone. Depending on the type of use, filling of the interstices with natural bone substance (spongy tissue) is possible. After resorption of the filler material, bone grows without interference around the individual spring-like fibers or wires. On the one hand, this increases the area of adhesion between bone and implant and, on the other hand, if the implant is encased without connective tissue, the natural bone establishes a connection between itself and the implant even if there is no chemical activity between them.

The orientation of the fibers or wires with respect to the surface of the implant bearing is adapted depending on the type of use. Regardless of how the fibers or wires come out of the implant surface, the fibers or wires must not cross over one another in any case since this interferes with the biological growth of the bone cells. If fibers or wires cross over one another, no total inclusion is assured, for example if unsystematic fiber arrangements exist or with conventional fiber bond structures as they are customary for glass fiber reinforced carbons, carbon fiber reinforced carbons and carbon fiber reinforced plastics.

The fibers or wires may be composed either of metallic substances or may be organic or inorganic fibers. If metallic materials are employed it may be provided, by way of an electroplating process, that the metallic fibers grow perpendicularly to the surface. The strength and elasticity of the fiber or wire material is adapted to the physiological requirements. The substance introduced into the implant on the side of the bone between the individual fibers or wires is composed either of inorganic or organic, partially or wholly resorbable, bioactive and/or osteogenesis inducing materials. The interface layer between the bone growing into the implant due to dissolution of the matrix and the remainder of the implant, i.e. the insoluble core of nonresorbable fiber bond material or metallic substances, may additionally be coated, on the side of the core, with a bioactive, wholly or partially not or difficultly resorbable material so as to increase adhesion between the natural bone and the implant. The bioactive, not or difficultly resorbable interface layer may produce additional anchorage between bone and implant by the provision of covalent bonds, i.e. an adhesive substance.

According to the object of the invention, the implant is to serve as a long-term implant, i.e. a lifelong bone substitute. Due to the special bond between bone and implant, physiological conditions can be realized particularly by maintaining a natural friction fit and the flow of forces resulting therefrom.

For artificial joint replacement, e.g. a hip socket, a healing process takes place when the bone grows into the implant, similar to that occurring for repair of a fracture, i.e. a firm, immovable connection is produced between bone and implant. Even if there are complications, e.g. infections or repeated surgery, the living bone tissue is not damaged beyond the original degree since not much bone needs to be excavated for a second implantation.

For implantations of tooth roots, selection of wire or fiber, i.e. its type and size, produces an elastic connection between tooth root implant and jaw bone that can be stressed with tension and pressure. Therefore, a purely cylindrical helix is particularly suitable not only for tooth root implants but also for other implants.

If a resorbable matrix is employed it is further possible to embed antibiotics in the latter.

Various possibilities exist for a firm connection of the wires or fibers with the core: for example, the wires or fibers may extend particularly into the core or may be fastened to the implant surface by means of an adhesive, or may be welded or sintered on.

Preferably the fibers are coated with a bioactive and/or osteogenesis inducing material before they are wound or compressed.

Advantageously a highly quenched substance having an extreme density of lattice imperfectons is used as the resorbable and/or osteogenesis inducing material.

However, the invention is not limited to such embodiments in which the implant core and the wires or fibers are made of one and the same material or material of the same type. Rather, the implant core and the wires or fibers may also be composed of different substances, such as, for example preferably for implants employing a plastic core and wires or fibers firmly embedded therein.

It is likewise recommended to employ implant materials in which electromagnetic stimulation accelerates bone and/or tissue growth and thus the healing process is shortened.

For dental implants (tooth root replacement), the tooth root implant may be equipped, until the defect has healed, with an additional anchorage, a primary fix, for better ingrowth. Advantageously, the primary fix is resorbed after defect healing is completed, i.e. after the fibers or wires are encased. In such a case, the coating of a resorbable bioactive and/or osteogenesis inducing substance could be omitted and the interstices between the individual springs, i.e. wires or fibers, could be filled with natural bone substance. In the simplest case, the primary fix can be effected by means of clips or retaining clamps which can be removed after the defect healing process.

Depending on the type of stress involved, it may not be necessary to employ a fiber of the same strength or wires or fibers of the same thickness and/or length if the occurring maximum stresses are small and no micromovement due to fiber geometry is possible, e.g. with spring-like helixes. Preferably, the different length wires or fibers are adapted to one another in such a way that under load they are approximately uniformly stressed over their length.

In exceptional cases, a wholly or partially resorbable matrix of inorganic and/or organic material may be omitted, particularly if the helixes or wires are short, are equipped with a core and, in spite of their flexible characteristics, have a basic rigidity (inherent stability). This is not possible with simple geometric fibers having the same diameter because they lack either the basic rigidity or the flexibility.

Proper growth between implant and bone requires a proper bond which can be assured only if the fibers cannot uncontrollably change their position with respect to the bone. It has also been found that fibers, which have the same diameter and are made of the same material over their entire length, exhibit increased stresses at the point where the fiber is clamped to the core. Micromovement also takes place between fiber and bone under stress if the E moduli are not adapted to one another. Particularly in implants having rigid transition structures, e.g. pins or superposed spheres, micromovement between bone and implant must be expected due to the differences in E moduli and thus, over a long period of time, destruction of the firm bond between bone and implant may occur. These drawbacks are eliminated by the present invention.

BRIEF DESCRIPTION OF THE DRAWING

Embodiments of the invention are illustrated in the drawings. It is shown in

FIGS. 1 to 7, sectional views of an implant including its fibers or wires projecting from the matrix.

DESCRIPTION OF THE PREFERRED EMBODIMENTS

Figure 7:
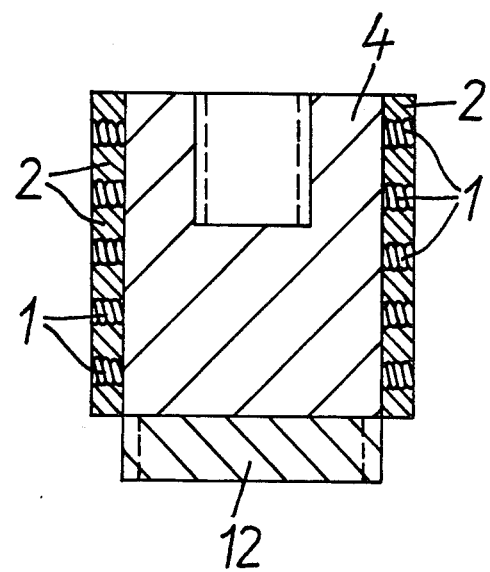

The implants for bone and tooth root replacement with special transition structure between bone and implant core and partially or completely resorbable matrix 2 on the side of the bone as shown in the above-mentioned figures are essentially composed of a core 4 of a metallic or composite fiber material and of permanently anchored, porcupine quill or brush-like metallic wires or fiber bond material fibers which preferably extend perpendicularly to the implant surface and are disposed in a matrix 2.

For example, FIG. 1 shows a metallic core 4 as well as cylindrical metal wires 1 fastened to the surface of the core, with the wires being fastened to an adhesive coated interface layer 3 at the surface of the core. Interstice 2 (the matrix) is filled with a wholly or partially resorbable, bioactive and/or osteogenesis inducing material.

In contrast thereto, in the embodiment according to FIG. 2, wires 5 have a conical shape. In both embodiments according to FIGS. 1 and 2, core 4 and the wires are formed uniformly of a single material, metal in the present case.

In contradistinction thereto, in the embodiment according to FIGS. 3 to 5, different materials are involved, namely metal on the one hand and a composite material on the other hand.

For example, in the implant shown in FIG. 3, helical composite material fibers 6 are fastened to a metallic core 4. The implant according to FIG. 4 is additionally provided with a core 7 which is surrounded by a helix 8 made of composite material and having a decreasing helix radius. This helix 8 as well as core 7 are both likewise fastened to the surface of the implant core.

It is possible to make core 7 and helix 8 surrounding it of the same or of different materials, with metals or composite materials being involved in each case.

The implant shown in FIG. 5 has helical metal wires 9 and 10, with the radius of the helix being uniform in the former case and becoming smaller in the latter case with increasing distance from implant core 4. It is additionally also possible to employ helixes having different diameters or helixes whose pitch is greater than or equal to the respective helix diameter. In particular, metal wires 9 and 10 extend until far into implant core 4 which is made of a composite material.

Finally, FIG. 6 shows pin-shaped fibers 11, each having a different length, which are fastened to an implant core of composite material.

Regardless of whether the wires or fibers in FIGS. 1 through 6 project from the implant surface with uniform or nonuniform spacing, individually or in groups, their spacing is selected in such a manner that the bone tissue between them can be properly supplied. FIG. 7 shows an implant for a tooth having a primary fix 12. Primary fix 12 is provided on the core 4 of the tooth root implant to enhance ingrowth of the implant into the jaw bone, the primary fix functioning as an additional anchorage for the implant, that is, as a primary fix or anchorage for the implant.

I claim:

1. Implant for bone and tooth root replacement, comprising a core and a matrix, which matrix is at least partially resorbable and is provided along at least a portion of the surface of the core, and which core is comprised of a material selected from the group consisting of a metallic material and a composite material, and is provided with a transition structure at least along the surface thereof which faces the bone or tooth root, the transition structure including a plurality of projecting members, which projecting members are flexible, have a helical shape, are comprised of a material selected from the group consisting of metal wires, organic fibers and inorganic fibers, are permanently anchored in the core, are surrounded by the matrix, and have a modulus of elasticity which corresponds to the modulus of elasticity of the bone tissue that will later surround same when the implant is implanted and the matrix is at least partially resorbed.

2. Implant according to claim 1, wherein on the side of the bone, the matrix is at least partially resorbable.

3. The implant according to claims 2, wherein the matrix is at least partially comprised of natural bone substance.

4. Implant according to claim 1, comprising a body-compatible substance selected from the group consisting of an organic substance, an inorganic substance, and mixtures thereof.

5. Implant according to claim 1, wherein the at least partially resorbable matrix is comprised of a material which is one or both of bioactive and osteogenesis-inducing.

6. The implant according to claim 5, wherein the at least partially resorbable matrix is selected from the group consisting of tricalcium phosphate, hydroxylapatite, and bioglass.

7. Implant according to claim 1, wherein the resorbable matrix contains at least one antibiotic.

8. Implant according to claim 1, wherein the projecting members have essentially uniform tension and strength over their length.

9. Implant according to claim 1, wherein projecting members exit from the surface of the core at irregular distances from one another.

10. The implant according to claim 9, wherein the projecting members exit from the surface of the core in groups, which groups are spaced apart from one another.

11. Implant according to claim 1, wherien the distance between the projecting members is selected so that bone tissue growth between adjacent projecting members can proceed without interference.

12. Implant according to claim 1, wherein the projecting members each has the same diameter.

13. Implant according to claim 1, wherein the projecting members have different thicknesses and lengths.

14. Implant according to claim 1, wherien the projecting members have a helical shape which is one of cylindrical, conical and parabolic.

15. Implant according to claim 14, wherein the projecting members have a coating provided thereon, which coating is comprised of a material which is one or both of bioactive and osteogenesis-inducing and is provided on the projecting members prior to imparting a helical shape thereto.

16. The implant according to claim 14, wherein the projecting members each has a helical pitch which is at least equal to diameter thereof.

17. Implant according to claim 1, wherein the projecting members are each provided with an individual core so as to absorb shear forces.

18. The implant according to claim 17, wherein said individual cores are fixed to the core of the implant.

19. Implant according to claim 1, wherein the projecting members each has a thickness which is less than 800 $\mu$m.

20. Implant according to claim 1, wherein the projecting members are fixed to the core.

21. Implant according to claim 20, wherein the projecting members extend into the core.

22. Implant according to claim 1, wherein the projecting members are fastened to the surface of the core by one of an adhesive, welding and sintering.

23. Implant according to claim 1, wherein the core and the projecting members are made of different substances.

24. The implant according to claim 23, wherein the core is a plastic core and the projecting members are firmly imbedded in the plastic core.

25. Implant according to claim 1, wherein an interface layer is provided between the core and the resorbable matrix and is comprised of a material which is one or more of resorbable, bioactive and osteogenesis-inducing.

26. Implant according to claim 25, wherein the interface layer is provided with an adhesive so as to covalently bond the core and the matrix.

27. Implant according to claim 25, wherein the material of the interface layer is a highly quenched substance having a substantial density of lattice imperfections.

28. Implant according to claim 1, for tooth root replacement in a jaw bone, wherein the core is provided with a primary fix to enhance ingrowth of the implant into the jaw bone, the primary fix functioning as an additional anchorage for the implant.

29. Implant according to claim 28, wherein the primary fix is comprised of a resorbable material.

30. Implant according to claim 1, wherein the implant is a tooth root implant adapted to be positioned in a jaw bone so that the plurality of projecting members constitute an elastic connection between the tooth root implant and the jaw bone, whereby the elastic connection simulates the tooth retention apparatus of a natural tooth after the tooth root implant has been positioned in the jaw bone and the jaw bone has grown around the transition structure.

31. The implant according to claim 1, wherein the matrix comprises particles which are resorbable and are embedded within the matrix.

32. The implant according to claim 1, wherien the projecting members extend perpendicularly outwardly from the surface of the implant.

33. Implant for bone and tooth root replacement, comprising a core and a matrix, which matrix is at least partially resorbable and is provided along at least a portion of the surface of the core, and which core is comprised of a material selected from the group consisting of a metallic material and a composite material, and is provided with a transition structure at least along the surface thereof which faces the bone or tooth root, the transition structure including a plurality of projecting members, which projecting members are flexible, have wavy shape, are comprised of a material selected from the group consisting of metal wires, organic fibers and inorganic fibers, are permanently anchored in the core, are surrounded by the matrix, and have a modulus of elasticity which corresponds to the modulus of elasticity of the bone tissue that will later surround same when the implant is implanted and the matrix is at least partially resorbed.

34. The implant according to claim 33, wherein the projecting members are arranged offset to one another.

* * * * *

UNITED STATES PATENT AND TRADEMARK OFFICE
CERTIFICATE OF CORRECTION

PATENT NO. : 4,772,203

DATED : September 20, 1988

INVENTOR(S) : Rüdiger Scheunemann

It is certified that error appears in the above-identified patent and that said Letters Patent is hereby corrected as shown below:

In the heading of the patent, please insert --[73] Assignee: Fried. Krupp Gesellschaft mit beschränkter Haftung, Essen, FEDERAL REPUBLIC OF GERMANY.--.

Signed and Sealed this

Seventh Day of February, 1989

*Attest:*

DONALD J. QUIGG

*Attesting Officer*  *Commissioner of Patents and Trademarks*